Figure 1:
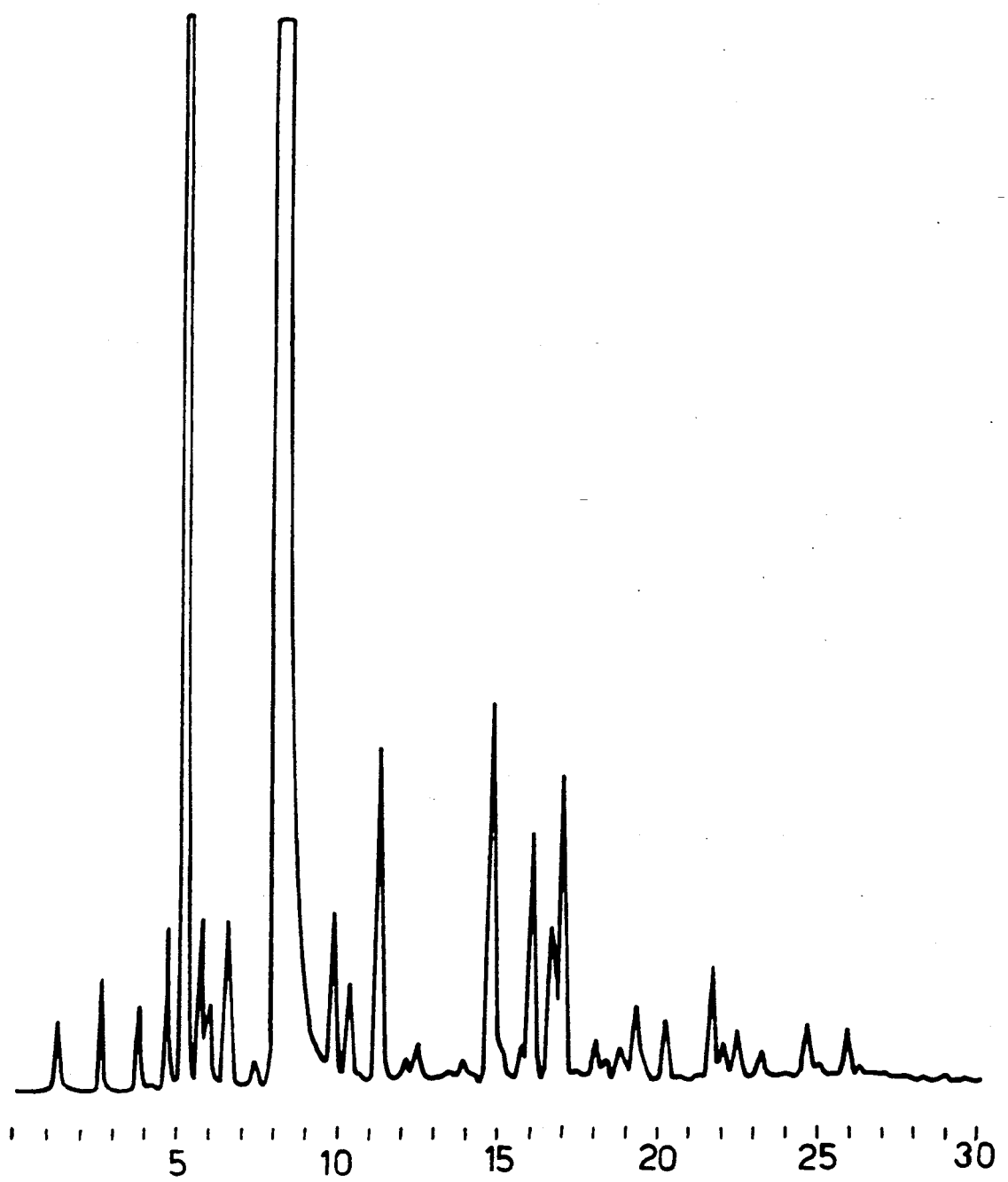

United States Patent [19]

Marzorati et al.

[11] Patent Number: 5,103,044

[45] Date of Patent: Apr. 7, 1992

[54] METHOD FOR PURIFYING LINURON

[75] Inventors: Carlo Marzorati, Segrate; Gian P. Marinelli, Cinisello Balsamo, both of Italy

[73] Assignee: I.Pi.Ci. S.p.A., Milan, Italy

[21] Appl. No.: 497,778

[22] Filed: Mar. 21, 1990

Related U.S. Application Data

[63] Continuation of Ser. No. 288,314, Dec. 22, 1988, abandoned, which is a continuation of Ser. No. 73,651, Jul. 15, 1987, abandoned.

[30] Foreign Application Priority Data

Nov. 27, 1986 [IT]  Italy ................................ 67884 A/86

[51] Int. Cl.$^5$ ................ C07C 275/32; C07C 273/16
[52] U.S. Cl. ...................................................... 560/313
[58] Field of Search .......................................... 560/313

[56] References Cited

U.S. PATENT DOCUMENTS 4,075,235  2/1978  Kühle et al. ...................... 560/313

OTHER PUBLICATIONS

Robertson et al., Lab. Practice of Org. Chem., 4th Ed., MacMillan Co., N.Y., 1962, p. 174.

*Primary Examiner*—Joseph Paul Brust
*Attorney, Agent, or Firm*—Sughrue, Mion, Zinn, Macpeak & Seas

[57] ABSTRACT

In order to remove traces of impurities constituted by tetrachloroazobenzene, tetrachloroazoxybenzene, polychlorinated diphenyl compounds and the like from crude linuron, the crude linuron is subjected to a single purification treatment of dissolution in a hot organic solvent and subsequent crystallization by cooling and recovery of the precipitated linuron. Preferred solvents are aromatic solvents, preferably chlorinated. The treatment enables the impurity content to be reduced to values less than 1 ppm.

6 Claims, 2 Drawing Sheets

METHOD FOR PURIFYING LINURON

This is a continuation of application Ser. No. 07/288,314 filed Dec. 22, 1988, abandoned, which is a continuation of application Ser. No. 07/073,651 filed Jul. 15, 1987, abandoned.

The present invention relates to a method for the purification of crude linuron, and particularly to a method adapted to achieve the substantial removal of the impurities tetrachloroazobenzene (TCAB), tetrachloroazoxybenzene (TCOB) polychlorinated diphenyl compounds (PCB) and the like from the crude linuron, these impurities being present in trace concentrations.

The presence has recently been found in linuron, a ureic herbicide having the chemical name N'-(3,4-dichlorophenyl)-N-methoxy-N-methylurea described in the MERCK index, Edition X as number 5336, of traces of TCAB, TCAOB and PCB, which have a suspected or ascertained carcinogenic action Typically the overall concentration of the three said components found in crude linuron obtained by the addition reaction of hydroxylamine and 3,4-dichlorophenyl isocyanate and subsequent alkylation with dimethyl sulphate does not exceed values of the order of 1000 ppm. By the term "traces" as used in the present description it is indeed intended to indicate concentrations of less than 1000 ppm.

Even though the competent authorities in the various countries in which linuron is used have not at present established a maximum admissible concentration for these compounds, it is desirable, in accordance with the maximum allowable concentrations for other compounds having suspected carcinogenic action, such as nitrosamines, to provide a method which enables these Z impurities to be removed to concentrations of less than 5 or preferably less than 1 ppm.

By the term "substantial" removal of the said compounds, as used in the present description, it is indeed intended to indicate a removal such as to give a maximum overall concentration at least less than 5 ppm.

The technical and chemical difficulties resulting from the need to achieve the simultaneous removal of impurities present even in trace quantities being taken into account, the object of the present invention is to provide a method for the substantial removal of the said impurities from linuron which can be carried out economically without having too harmful an effect on the production costs.

Surprisingly it has now been discovered that this and other objects, which will become apparent from the description which follows, may be achieved by a method characterised in that the crude linuron is subjected to a single purification treatment comprising its dissolving in a hot organic solvent added to the linuron in sufficient quantities to achieve its dissolution and subsequent crystallisation of the linuron from the solvent by cooling and recovery of the crystallised linuron.

The method of the invention may be applied directly as the final stage in the method for the production of linuron which results in the linuron being obtained as a wet paste. In this case, the wet linuron paste is preferably previously dispersed in water at ambient temperature to obtain a fluid dispersion to which the organic solvent is added and which is heated to facilitate the dissolution of the linuron itself. It has also been found that the presence of water facilitates the handling of the linuron after the crystallisation of the linuron.

The solvents used in the method are preferably aromatic solvents, preferably chlorinated, such as chlorotoluene, chlorobenzene and xylene. Aliphatic hydrocarbons in which linuron is slightly soluble could however also be used, these being for example octane and oxygenated aliphatic hydrocarbons such as methyl ethyl ketone. The use of these latter solvents results in a series of disadvantages which leads to lower recoveries and poorer selectivity with regard to all the impurities.

The preferred solvent is orthochlorotoluene (OCT) which has advantages by virtue of its high solvating power towards the linuron which enables smaller volumes of the solvent to be used. In the case of the use of OCT, the OCT/linuron ratio (volume in litres/weight in kilograms) is preferably between 1 and 0.6.

The crystallisation of the linuron from the solvent takes place without the need for seeding and its recovery is carried out easily by filtration. The recovery yield from a 100% loading of linuron is very high, typically greater than 94%.

The cake is preferably subjected to repeated washing with the solvent itself in order to remove the mother liquors. Furthermore the solvents may be recycled several times without purification for treating successive batches of linuron, with further improvement in the yield and without harmful effects on the quality.

The technical linuron used in the experimental tests carried out by the applicants was obtained by the process comprising the addition reaction of 3,4-dichlorophenyl isocyanate with hydroxylamine and the subsequent alkylation reaction with dimethyl sulphate in water and typically gives a quantity of linuron determined by the hydrolysis method of the order of 96% and of the order of 92% when determined by HPLC analysis.

Analysis carried out on technical linuron by HPLC -Iso indicates the presence of the corresponding monoalkylate derivative in concentrations of the order of about 3 to 5% by weight, a large number of impurities resulting from the production process such as, for example, ureic derivatives present in concentrations of the order of from 0.1 to 1%. Following the purification treatment of the invention, the concentration of most of these impurities is reduced to values below the sensitivity threshold of the HPLC instrument and the concentration of the few remaining impurities is reduced to values of less than 0.1%. The concentration of the monoalkylate is reduced by at least 50% with a consequent increase in the content of purified linuron to 98% minimum HPLC. This obviously constitutes a further advantage of the method of the invention.

As a result of the treatment, the specific concentration of the impurities PCB, TCAB and TCAOB determined by mass spectrometry on the purified linuron is always less than 1 ppm. In particular, and this is extremely surprising, concentrations have been obtained for each of the said impurities of less than 0.1 ppm, or less than the limit of sensitivity of the HPLC analysis apparatus.

Further characteristics and advantages of the method of the invention will become apparent from the examples which follow.

EXAMPLE 1

290 kg of a wet paste of technical linuron having a moisture content of 23% by weight are loaded into dissolving vessel provided with an agitator and a heat exchange jacket. The HPLC chromatogram of the linuron used is illustrated in FIG. 1. Table 1 gives the retention times and concentrations, standardised to 100% for the components corresponding to the peaks in FIG. 1. In the cromatogram, the linuron corresponds to the peak having a retention time of 8.38 and the monoalkylate derivative corresponds to the peak having a retention time of 5.37. The quantity of the main active ingredient in the linuron used determined by HPLC is 93.4%. The concentrations of PCB, TCAB and TCAOB determined by mass spectrometry are as follows:

| | |
|---|---|
| PCB | 52.6 ppm |
| TCAB | 117.2 ppm |
| TCAOB | 12 ppm |

350 litres of water are introduced under agitation into the dissolving vessel at ambient temperature and then 177 litres of OCT are added, still under agitation, the ratio of the volume of OCT (litres)/dry linuron (kg) thus being 0.8. The temperature is brought to 70° C. until the linuron has dissolved completely.

The 2-phase dispersion obtained is fed to an agitated closed crystallisation vessel provided with a heat exchange jacket and then cooled to a temperature of 0° C. The crystallisation of the linuron starts spontaneously at a temperature of about 40° C.

The crystalline product extracted from the crystallisation vessel is filtered and washed with 30 litres of OCT. Two further washings are then carried out with the same quantities of OCT followed by a washing with 100 litres of water.

After each washing a sample of linuron is analysed for impurities, the following values being obtained.

| | PCB (ppm) | TCAB (ppm) | TCAOB (ppm) |
|---|---|---|---|
| 1st washing | 1.5 | 3 | 0.3 |
| 2nd washing | 1 | 1.2 | n.d |
| 3rd washing | n.d. | n.d. | n.d. | n.d = not determinable (less than the threshold of sensitivity of the analysis apparatus (0.2 ppm)).

The product obtained after the washings, having a moisture content of 23%, is then dried. The HPLC titre of the active principle was 98.5%.

Figure 2:
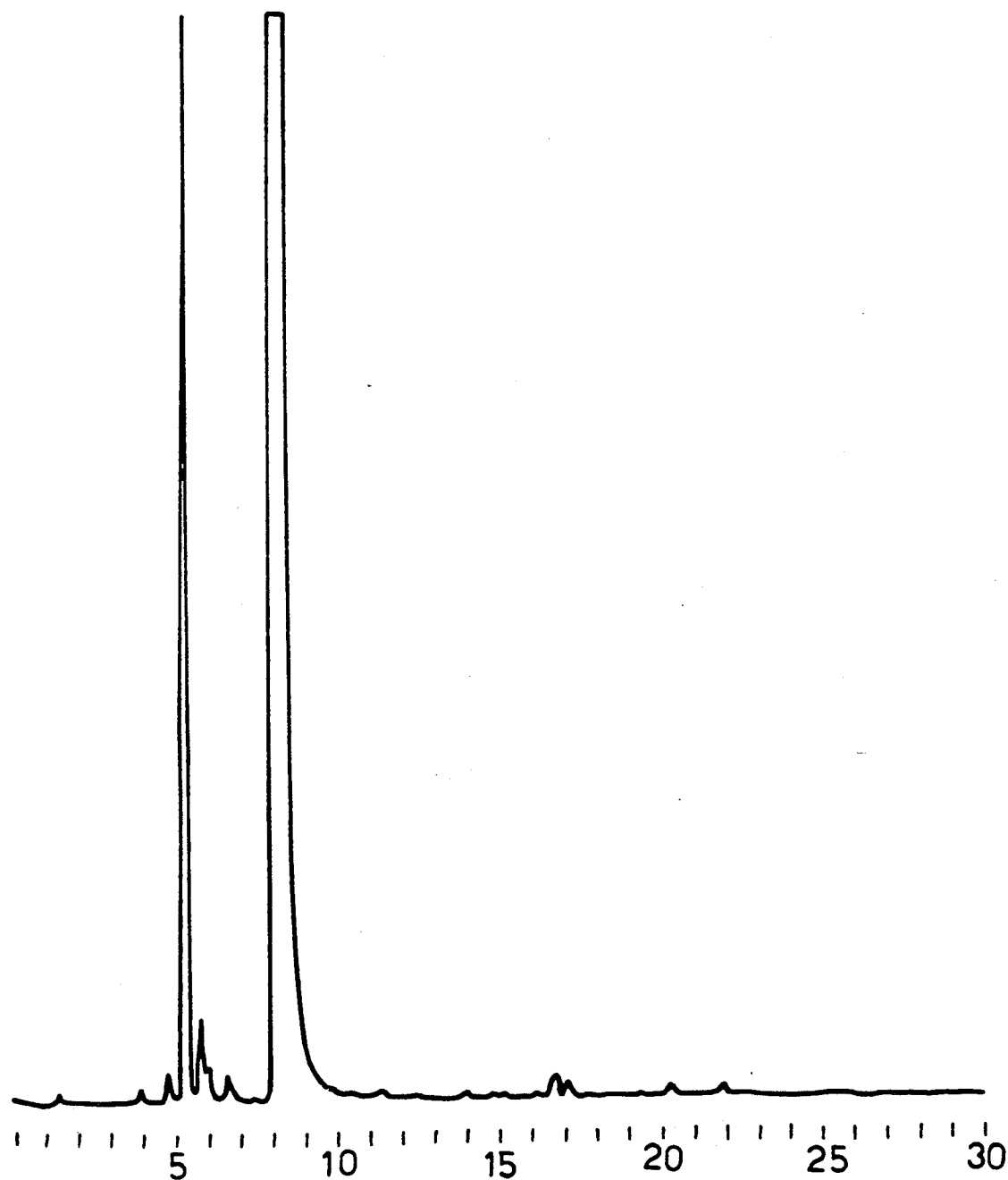

FIG. 2 illustrates the HPLC chromatogram of the purified linuron obtained under the same conditions as those of the chromatogram of FIG. 1.

Table 2 gives the retention times and concentration percentages standardised to 100 for the peaks identified, the concentration of which is greater than the range of sensitivity of the integrator. It may be seen that the concentration of all the impurities present initially is reduced to values less than 1000 ppm.

In total 199 kg of dry linuron are recovered which represent a yield of 94% expressed as a ratio of 100% dry linuron obtained to 100% dry linuron loaded in.

TABLE 1

| SAMPLE: TECHNICAL LINURON OF EXAMPLE 1 CHROMATOGRAM OF FIG. 1 | | |
|---|---|---|
| PEAK NO | RETENTION TIME | CONCENTRATION |
| 1 | 1.41 | 0.083 |
| 2 | 2.76 | 0.088 |
| 3 | 3.93 | 0.117 |
| 4 | 4.84 | 0.199 |

TABLE 1-continued

| SAMPLE: TECHNICAL LINURON OF EXAMPLE 1 CHROMATOGRAM OF FIG. 1 | | |
|---|---|---|
| PEAK NO | RETENTION TIME | CONCENTRATION |
| 5 | 5.37 | 2.264 |
| 6 | 5.87 | 0.285 |
| 8 | 6.66 | 0.358 |
| 10 | 8.38 | 91.951 |
| 11 | 9.95 | 0.270 |
| 12 | 10.48 | 0.171 |
| 13 | 11.40 | 0.625 |
| 15 | 12.64 | 0.080 |
| 18 | 14.87 | 0.875 |
| 20 | 16.15 | 0.505 |
| 21 | 16.76 | 0.293 |
| 22 | 17.06 | 0.652 |
| 24 | 18.14 | 0.085 |
| 26 | 18.90 | 0.096 |
| 27 | 19.41 | 0.193 |
| 28 | 20.38 | 0.131 |
| 29 | 21.81 | 0.320 |
| 31 | 22.61 | 0.100 |
| 34 | 24.78 | 0.119 |
| 36 | 26.05 | 0.116 |
| TOTAL | | 100,000 |

TABLE II

| SAMPLE; PURIFIED LINURON OF EXAMPLE 1 CHROMATOGRAM OF FIG. 2 | | |
|---|---|---|
| PEAK NO. | RETENTION TIME | CONCENTRATION |
| 4 | 5.28 | 1,840 |
| 5 | 5.78 | 0.173 |
| 9 | 8.26 | 97.986 |
| TOTAL | | 100.000 |

EXAMPLE 2

The test of example 1 is repeated with 298 kg of technical linuron paste with a moisture content of 25% and an active principle content of 93.2 being loaded into the dissolving vessel, the paste having the following concentrations of PCB, TCAB and TCAOB:

| | |
|---|---|
| PCB | 79.9 ppm |
| TCAB | 109 ppm |
| TCAOB | 10 ppm |

324 litres of water are introduced into the vessel followed, under agitation, by 230 litres of the solvent OCT already used in the purification of example 1 and including the washings without prior purification, the temperature then being brought to 65° C. The mass is then cooled to a temperature of about 0° C. and the crystallised linuron product is subjected to three washings with 30 litres of OCT and finally with 100 litres of water.

Analysis carried out on the linuron samples taken after each washing gave the following contents of the impurities PCB, TCAB and TCAOB.

| | PCB (ppm) | TCAB (ppm) | TCAOB (ppm) |
|---|---|---|---|
| 1st washing | 5.1 | 8.2 | 0.8 |
| 2nd washing | 1.3 | 1.7 | n.d. |
| 3rd washing | 0.3 | n.d. | n.d. |

A total of 207.4 kg of the dry linuron is recovered with an HPLC titre of 98.2% with a yield calculated as in Example 1 of 98%.

The test is repeated 5 times with the use of the same quantities of linuron having the same content of impurities and the same quantities of solvent the recycled solvent from the test described above being used again. Even after these tests the overall content of the impurities PCB, TCAB and TCAOB is reduced to a total value which is always less than 3 ppm in each case.

It is understood that the principle of the invention remaining the same, the modes of embodiment and details of realisation may be varied widely with respect to that described and illustrated purely by way of non-limiting example.

We claim:

1. A method for the substantial purification of crude linuron containing a total concentration of less than 1,000 ppm of impurities comprising tetrachloroazobenzene, tetrachloroazoxybenzene and polychlorinated diphenyl compounds to reduce the concentration of each single impurity that is present to less than 5 ppm, the method consisting of a single recrystallization stage comprising dissolving the said crude linuron in a hot chlorinated aromatic organic solvent selected from the group consisting of chlorotoluene and chlorobenzene, subsequently crystallizing the linuron from the solvent by cooling, recovering the crystallized linuron and washing the thus recovered linuron, which linuron contains less than 5 ppm of each single impurity that is present.

2. A method according to claim 1, in which the crude linuron is a moist paste, the method including the step of adding a quantity of water to the paste to obtain a fluid dispersion before the dissolution in the solvent.

3. A method according to claim 1, wherein the solvent is orthochlorotoluene which is added to the mass of crude linuron in a ratio of orthochlorotoluene to linuron of between 1 and 0.6 (volume (litre/weight (kg)).

4. A method for the preparation of linuron substantially free from impurities comprising tetrachloroazobenzene, tetrachloroazoxybenzene and polychlorinated diphenyl compounds, the method comprising the addition reaction of 3,4-dichlorophenyl isocyanate and hydroxylamine and subsequent alkylation of the reaction product with dimethyl sulphate in water with recovery of a moist paste of linuron from the reaction mixture, wherein the paste is subject to a single purification treatment comprising dissolving the said paste in a hot chlorinated aromatic organic solvent selected from the group consisting of chlorotoluene and chlorobenzene added to the paste in a sufficient quantity to achieve at least partial dissolution of the paste, subsequent crystallization of the linuron from the solvent by cooling, recovery of the crystallized linuron and washing the thus recovered linuron, which linuron contains less than 5 ppm of each single impurity that is present.

5. A method according to claim 4, further including the step of adding a quantity of water to the moist paste sufficient to obtain a fluid dispersion.

6. A method according to claim 4, wherein the solvent is orthochlorotoluene which is added to the mass of crude linuron in a ratio of orthochlorotoluene to linuron of between 1 and 0.6 (volume (litre/weight (kg)).

* * * * *